United States Patent [19]
Vander Heyden

[11] Patent Number: 5,226,728
[45] Date of Patent: Jul. 13, 1993

[54] METHOD AND APPARATUS FOR MEASURING MASS FLOW AND ENERGY CONTENT USING A DIFFERENTIAL PRESSURE METER

[75] Inventor: William H. Vander Heyden, Mequon, Wis.

[73] Assignee: Badger Meter, Inc., Milwaukee, Wis.

[21] Appl. No.: 787,188

[22] Filed: Nov. 4, 1991

[51] Int. Cl.⁵ .................. G01N 25/22; G01F 9/00; G01F 1/00
[52] U.S. Cl. .......................... 374/36; 374/37; 73/196; 73/863.03; 73/863.61
[58] Field of Search ............ 374/36, 37; 73/196, 73/863.03, 863.61

[56] References Cited

U.S. PATENT DOCUMENTS

| | | | |
|---|---|---|---|
| 1,924,468 | 8/1933 | Stone | 73/196 |
| 2,067,645 | 1/1937 | Pinkerton | 374/37 |
| 2,263,335 | 11/1941 | Heinz | 374/37 |
| 2,574,665 | 11/1951 | Schuller | 374/37 |
| 3,525,259 | 8/1970 | Stough | 73/196 |
| 3,777,562 | 12/1973 | Clingman | 374/37 |
| 4,062,236 | 12/1977 | Clingman | 374/37 |
| 4,125,018 | 11/1978 | Clingman | 374/37 |
| 4,125,123 | 11/1978 | Clingman | 374/37 |
| 4,175,433 | 11/1979 | Rikuta | 73/196 |
| 4,285,245 | 8/1981 | Kennedy | 73/861 |
| 4,396,299 | 8/1983 | Clingman et al. | 374/37 |
| 4,446,748 | 5/1984 | Clingman et al. | 73/863.03 |
| 4,527,435 | 7/1985 | Hall et al. | 73/863.03 |
| 4,562,744 | 1/1986 | Hall et al. | 73/861.02 |
| 4,677,841 | 7/1987 | Kennedy | 73/30 |
| 4,706,492 | 11/1987 | Jones, Jr. et al. | 73/196 |
| 5,016,482 | 5/1991 | Clingman et al. | 73/863.61 |

FOREIGN PATENT DOCUMENTS

| | | | |
|---|---|---|---|
| 0664033 | 5/1979 | U.S.S.R. | 73/196 |
| 0652805 | 5/1951 | United Kingdom | 374/37 |
| 2099589 | 12/1982 | United Kingdom | 374/36 |

Primary Examiner—William A. Cuchlinski, Jr.
Assistant Examiner—Diego F. F. Gutierrez

[57] ABSTRACT

A method and apparatus for monitoring in real time the mass and energy flow rate of a gas through a pipeline. The invention determines the ratio of the mass flow rate of pipeline gas flowing through a pipeline compared to the mass flow rate of sample gas tapped from the pipeline line. The invention involves tapping sample gas from the pipeline and flowing the sample gas to a capillary tube or a similar device for creating a pressure differential in a small flow. The sample gas is maintained at substantially the same temperature as the gas in the pipeline while the sample gas is in the capillary tube. The sample gas flows through the capillary tube continuously as controlled by a flow controller at a rate that is independent of the pipeline gas flow rate. A differential pressure cell measures the pressure differential of the sample gas across the capillary tube and also measures the pressure differential of the pipeline gas across an orifice in the pipeline. The mass flow ratio of the pipeline gas flowing through the pipeline to the sample gas flowing through the capillary tube is computed using the pressure differentials measured by the differential pressure cell. The energy content of the pipeline gas is determined by measuring the energy content of the sample gas and relating that value to the mass flow ratio of the pipeline gas compared to the sample gas. If the sample gas is a saturated hydrocarbon and is burned with air at maximum flame temperature, the energy content of the pipeline gas stream is mathematically related to the mass flow rate of the air and the mass flow ratio of the pipeline gas compared to the sample gas.

29 Claims, 4 Drawing Sheets

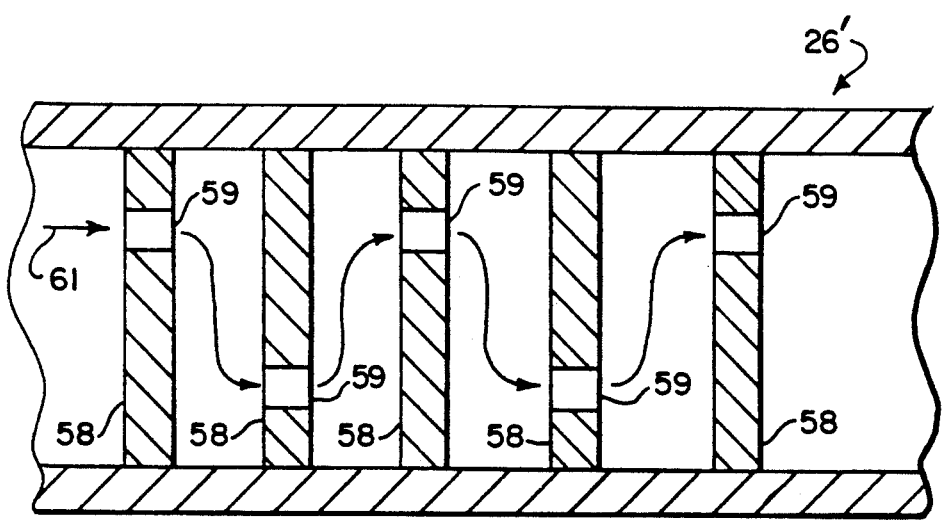
FIG. 3
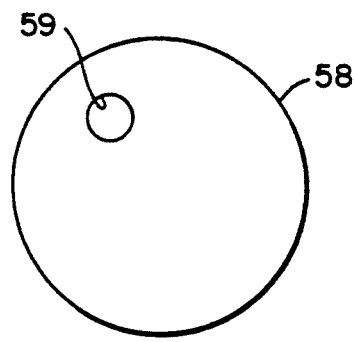
FIG. 4
FIG. 5
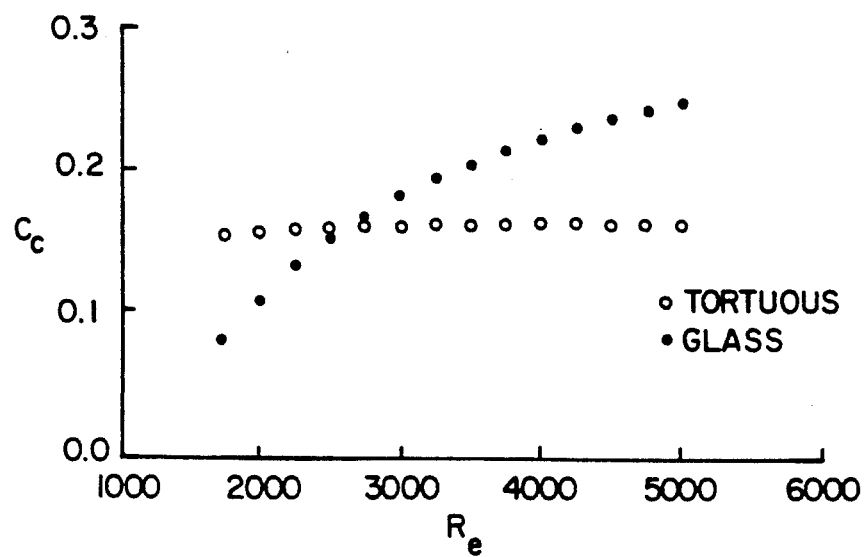

METHOD AND APPARATUS FOR MEASURING MASS FLOW AND ENERGY CONTENT USING A DIFFERENTIAL PRESSURE METER

BACKGROUND OF THE ART

The present invention relates to instrumentation for measuring in real time the mass and the energy flow rate of gas through a pipe. In particular, it relates to apparatus for measuring the ratio of the mass flow rate of pipeline gas flowing through a pipeline compared to sample gas flowing through the apparatus. It also relates to apparatus for measuring the energy flow rate of gas through a pipeline.

Mass and energy flow rates of gas through pipelines are normally calculated by flow computers from contemporaneous measurements of several gas parameters. Generally, for measuring mass flow rate, the volumetric flow rate of the pipeline gas is measured and gas temperature, pressure, and composition are measured to enable the gas density and, thus, the mass flow rate to be calculated from the volumetric flow rate. The composition of the gas is normally measured by gas chromatography. When the operating conditions are such that the supercompressibility of the gas in the calculation of density cannot be ignored, supercompressibility properties are estimated from either the virial equations of state for the gas or from precalculated correlations such as NX-19.

Knowledge of the values of the virial coefficients of particular gas compositions is quite limited in the art, so the calculation of gas density from the virial equations of state is not always possible. Furthermore, correlations such as NX-19, for natural gas, are approximate and the accuracy of extrapolations from such correlations is questionable. It is therefore difficult to obtain accurate real time density values for calculating the mass flow rates of gas flowing through a pipeline with present day equipment.

When energy flow rate, in addition to the mass flow rate, is desired, the energy content of the gas must also be determined. The energy content of the gas (energy per unit mass or volume) can be determined either indirectly by measuring the composition of the gas or by direct measurements such as the stoichiometric ratio method. Once the energy content of the gas is determined, the energy flow rate of the gas through the pipeline can be calculated by multiplying the energy content of the gas (e.g. BTU/lb) by the mass flow rate of the gas (e.g. lbs./hr).

Each of the measurements discussed above (volumetric flow, temperature, pressure, and composition) are measured separately and introduce an opportunity for measurement error. The aggregation of these measurement errors can substantially distort mass and energy flow calculations. To minimize measurement errors, each piece of instrumentation must be maintained and calibrated periodically. Moreover, additional errors can be introduced within the flow computer from calculations or inaccurate formulas or correlations.

In U.S. Pat. No. 4,396,299, Clingman discloses a method and apparatus for measuring the rate of energy flow of gas through a pipeline. The Clingman invention, which flows sample gas through a calibrated capillary tube, is able to measure the energy flow of pipeline gas through a pipeline by sampling a constant fraction of the pipeline gas and measuring the mass flow of air which is burned with the sample gas at maximum flame temperature. In the Clingman invention, the mass flow rate of the sample gas varies in direct proportion with the mass flow rate of the gas through the pipeline. This direct variation is the basis for at least two shortcomings of the device disclosed in U.S. Pat. No. 4,396,299.

A first shortcoming is caused by fluctuating sample gas flow. The fluctuations cause difficulties in burning the sample gas to measure its energy content. In the Clingman invention, the sample gas must be burned with air at maximum flame temperature so that the energy content of the sample gas flow is proportional to the air mass flow. If the mass flow of the sample gas varies over a wide range, the flame is not always stable and temperature detection may be corrupted. If this happens, the measured energy content of the sample gas will not be accurate.

A second shortcoming caused by the direct variation of sample gas flow to pipeline gas flow is practical in nature. In the United States, large natural gas pipelines are normally metered using multiple parallel metering runs so that monitoring the flow through large diameter pipes (i.e. >12") is avoided. In Clingman's invention, each of the multiple runs must be treated as an individual independent energy flow rate measurement since the Clingman invention requires that the sample gas flow rate be proportional to the flow rate of the gas flowing through each pipe being monitored.

SUMMARY OF THE INVENTION

The present invention is a method and apparatus for determining the ratio of the mass flow rate of pipeline gas through a pipeline compared to the mass flow rate of sample gas tapped from the pipeline. The invention allows this determination to be made in real time.

Sample gas is tapped from the pipeline and flows to a capillary tube, or similar device for producing a pressure differential. While the sample gas is in the capillary tube, the sample gas must be maintained at substantially the same temperature as the gas in the pipe. Sample gas flows through the capillary tube continuously as controlled by a flow controller at a rate independent of the pipeline flow rate.

The present invention requires two measurements for determining the mass flow ratio: a pressure differential of the pipeline gas across an orifice located in the pipeline, $\Delta P_o$, and a pressure differential of the sample gas across the capillary tube, $\Delta P_c$.

Based on the pressure differential of the sample gas across the capillary tube, $\Delta P_c$, and the pressure differential of the pipeline gas across an orifice or similar device producing a pressure differential in the pipeline, $\Delta P_o$, the ratio of the mass flow rate of pipeline gas through the pipeline compared to the mass flow rate of the sample gas can be computed in a control system (e.g. a computer).

The present invention alleviates the need to consider the effects of gas supercompressibility, temperature, pressure, density or composition because the sample gas pressure differential is measured while the sample gas is at pipeline conditions.

An object of the present invention is to measure the mass flow ratio without fluctuating the flow rate of the sample gas through the capillary tube. The present invention accomplishes this object by maintaining a flow through the capillary tube independent of the pipeline flow with a flow controller.

Another object of the present invention is to accurately measure the mass flow ratio without employing additional instrumentation to directly monitor the absolute temperature and absolute pressure of the pipeline gas. The present invention accomplishes this object by manipulating and monitoring the sample gas flow so that parameters necessary to accurately determine the mass flow ratio can be computed. For instance, the invention contemplates using a tortuous path capillary tube (or other apparatus which will, like the tortuous path capillary tube, have discharge characteristics at operating Reynold's Numbers similar to the discharge characteristics of the orifice in the pipeline) and periodically varying the sample gas molar flow rate between two preselected rates. In this manner, the ratio of the discharge coefficient for the orifice, $C_o$, compared to the capillary tube discharge coefficient, $C_c$, can be computed. The invention also contemplates using a second tortuous path capillary tube downstream in the sample gas flow of the first tortuous path capillary tube. With this configuration, the absolute pipeline pressure, $P_o$, and thus the ratio of the expansion factor for the pipeline gas, $Y_o$, compared to the sample gas expansion factor, $Y_c$, can be computed. Both ratios $(Y_o/Y_c)=Y_r$ and $(C_o/C_c)=C_r$ are parameters that can then be used to accurately determine the mass flow ratio.

The present invention also contemplates using the apparatus described above with apparatus for measuring the energy content of the sample gas to determine the energy flow rate of combustible gas through a pipeline.

After the sample gas exits the flow controller, it can be fed to a burner and burned with air at the maximum flame temperature. When the flame burns at the maximum flame temperature, the energy flow rate of the sample gas is proportional to the mass flow rate of air burning the sample gas.

The energy content of the flow of pipeline gas through the pipeline is determined from calculations involving the air mass flow rate, the pipeline gas pressure differential across the orifice and the sample gas pressure differential across the capillary tube. Each of these measurements can be made with precision.

The present invention allows accurate real time determination of the energy flow rate of a pipeline gas through a pipeline without the need to compensate for the effects of gas temperature, pressure, density, composition or supercompressibility. It also allows for the energy flow rate to be monitored accurately without substantially interfering with the pipeline gas flow.

Another object of the present invention is to provide measurement stability of the flame temperature and thus assure that the flame temperature is maximized and that the flow of air burning the sample gas is proportional to the energy content of the sample gas for saturated hydrocarbon gases. This object is accomplished by feeding the sample gas to the burner at a substantially constant flow rate and thereby promoting the flame to burn at the constant height. A thermocouple measuring the flame temperature can therefore be located in a consistent position within the flame and measure relative flame temperature more accurately.

Yet another object of the present invention is to measure the energy flow rate through each of the multiple pipeline runs at a metering station with a single meter. The present invention can accomplish this object by systematically sampling each run sequentially in time. This mode of operation is not possible with the Clingman invention because the Clingman invention requires that the sample gas flow rate be proportional to the flow rate of the gas flowing through each pipe being monitored; whereas, the present invention has no such requirements.

The foregoing objects and advantages of the present invention will appear from the following description. In the description, references are made to the accompanying drawings which form a part hereof and in which a preferred embodiment of the present invention is shown by way of illustration. Such embodiment does not necessarily represent the full scope of the invention, however, and reference must be made therefor to the claims for interpreting the scope of invention.

BRIEF DESCRIPTION OF THE DRAWINGS

FIG. 3 is a sectional view of a tortuous path capillary tube;

FIG. 4 is a front view of an obstruction disc;

FIG. 5 is a plot of test data showing the capillary tube discharge coefficient ($C_c$) as a function of Reynold's Number (Re);

DESCRIPTION OF THE PREFERRED EMBODIMENT

Figure 1:
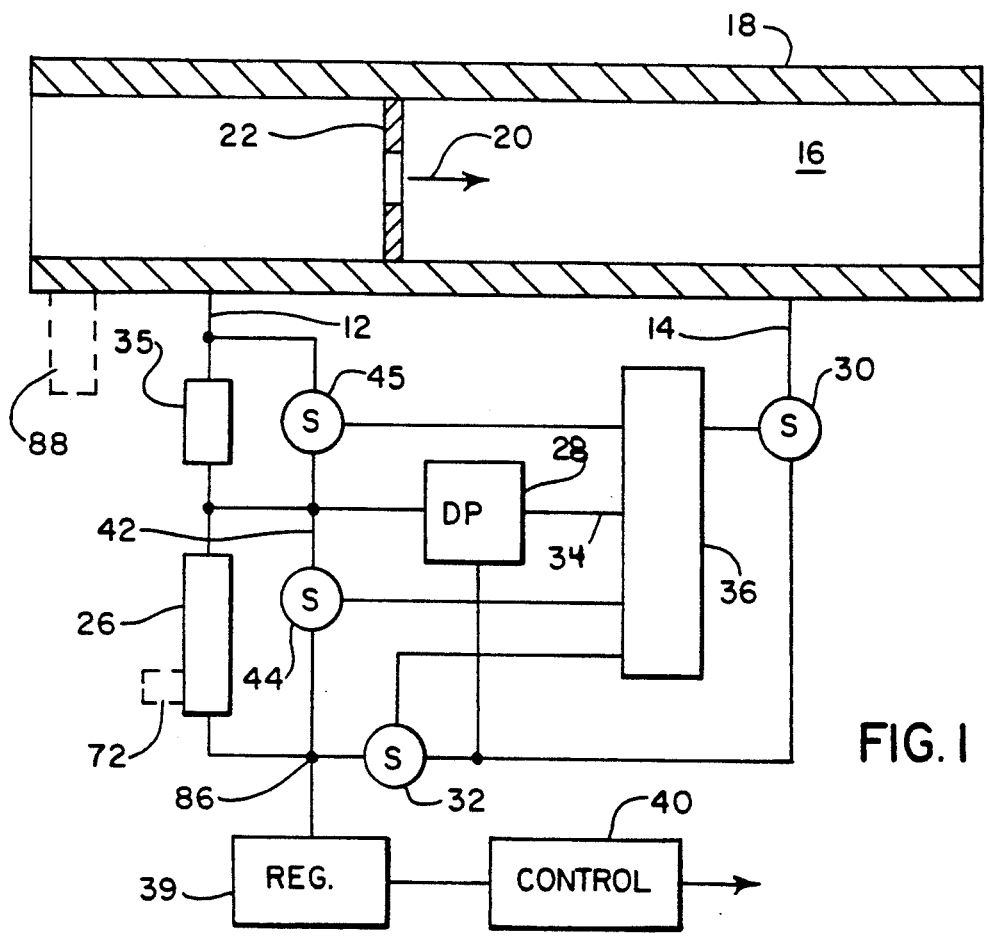
FIG. 1 is a schematic drawing showing the fundamental apparatus of the present invention.

Referring to FIG. 1, the present invention has a first 12 and a second port 14 for tapping pipeline gas 16 flowing through a pipeline 18 in the direction shown by arrow 20. The pipeline 18 typically has an internal orifice 22 and the pressure of the pipeline gas 16 changes as it flows across the orifice 22. Other differential pressure volumetric flow monitoring devices that produce a pressure differential and can be calibrated, including but not limited to venturi devices or nozzles, can be used in place of an internal orifice 22, but an internal orifice is preferred.

Figure 2:
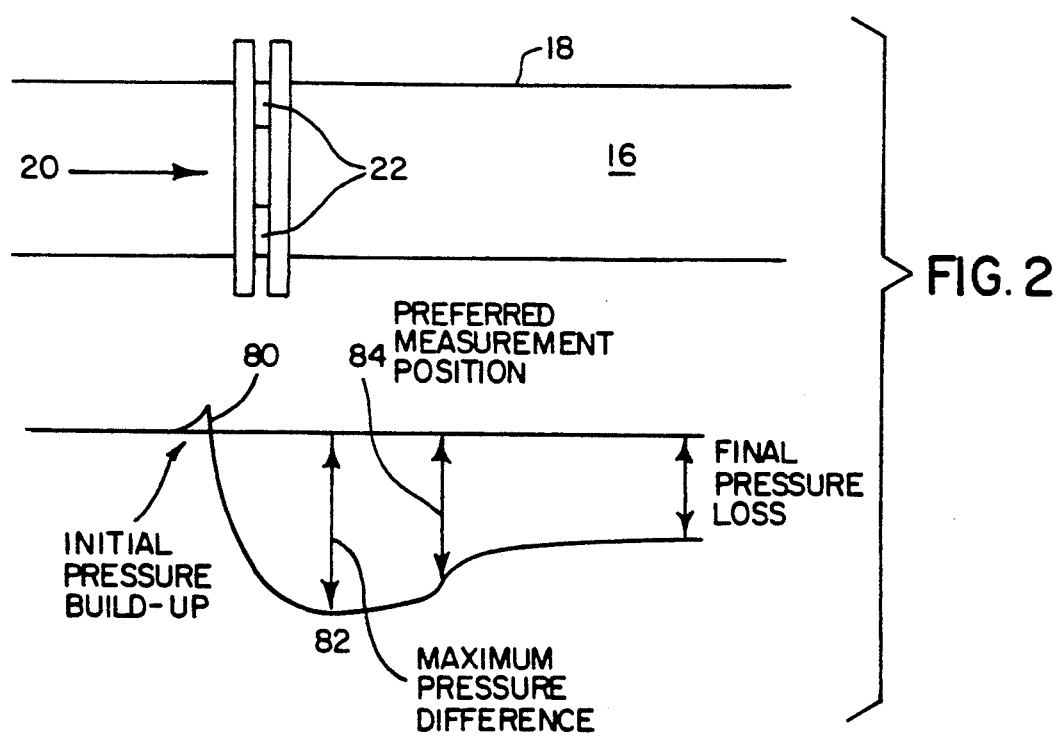
FIG. 2 is a schematic diagram depicting the dynamic nature of pressure differentials in pipeline gas flow.

It should also be noted that pressure differentials of pipeline gas 16 across an orifice 22 or other such device is dynamic in nature, and not necessarily constant as depicted in FIG. 2. In FIG. 2, as the flow 20 of the pipeline line gas 16 approaches the orifice 22, the gas pressure rises 80 slightly. The flow 20 is constricted to flow through the orifice 22 and continues to constrict after it passes through the orifice until it reaches a low pressure point 82. As the flow 20 constricts, flow speed increases and consequently the flow pressure drops. Flow pressure also drops due to frictional losses. As the flow 20 widens to fill the pipeline 18 downstream of the low pressure point 82, flow speed reduces and gas pressure recovers to a value equal to the initial flow pressure, $P_o$, less frictional losses. Differential pressure flow meters are most sensitive if the pressure differential measured is the initial pipeline pressure, $P_o$, less the pressure at the low pressure point 82. The physical location of the low pressure point 82, however, varies significantly with flow velocity and it is therefore preferred to monitor the flow pressure at an intermediate flow recovery point 84, because such a measurement is less likely to be inaccurate due to fluctuations in flow velocity. In the art, there are three kinds of taps for measuring pressure differentials, each for measuring the pressure at various stages after an orifice: flange taps, vena contracta taps, and pipe taps. It should be emphasized, however, that the present invention can be used with any type of differential pressure flow meter, including but not limited to an orifice plate 22, venturi, or nozzle, and without regard to the specific pressure difference which is monitored by the meter.

Referring to FIG. 1, the first port 12 taps sample gas 24 from the pipeline before it flows through the orifice 22. This sample gas 24 is routed to a capillary tube 26. Capillary tubes are made in many forms and the term capillary tube as used herein means a device for obtaining a very small controlled flow rate. As will be apparent to one skilled in the art, the present invention does not require that the capillary tube 26 be a conventional capillary tube, or a tortuous path capillary tube 26' described below. Rather, any apparatus that allows the flow of sample gas 24 and produces a pressure differential is sufficient for the present invention.

It is preferred, however, that the capillary tube 26 be a tortuous path capillary tube 26' as shown in FIGS. 3 and 4. Referring to FIGS. 3 and 4, the flow of sample gas 24 through the tortuous path capillary tube 26' is in the direction shown by arrows 61. The sample gas 24 is not able to flow through the tortuous path capillary tube 26' as straight-line, laminar flow because flow obstruction discs 58 obstruct the flow 61. Sample gas 24 can flow through the tortuous path capillary tube 26' only by flowing through flow holes 59 which extends through each obstruction disc 58. Each flow hole 59 is eccentrically located on a disc 58 and misaligned with adjacent flow holes 59 to create a tortuous flow path through the capillary tube 26'. A tortuous path capillary tube 26' with this sort of configuration has a more stable discharge coefficient, $C_c$, in the flow regime of interest as shown in FIG. 5. Testing has shown that it is preferred that the obstruction discs 58 be 0.060" thick and that the flow holes 59 have a 0.010" diameter. The obstruction discs 58 should be spaced apart a distance at least 5 to 6 times the thickness of the discs 58.

Referring again to FIG. 1, the second port 14 taps gas from the pipeline 18 after it flows through the orifice 22.

A differential pressure cell (DP cell) 28 measures a pipeline gas 16 pressure differential across the orifice 22, $\Delta P_o$, and a sample gas 24 pressure differential across the capillary tube 26, $\Delta P_c$. The DP cell accomplishes this by (i) measuring the pressure difference between the sample gas 24 before it flows through the capillary tube 26 and the pipeline gas 16 after it flows through the orifice 22 or (ii) measuring the sample gas 24 after it flows through capillary tube 26.

A first solenoid valve 30 is located between the DP cell 28 and the second port 14 of the flow splitting device. A second solenoid valve 32 is located between the DP cell 28 and the capillary tube 26 outlet 38. A control system 36 communicates to the first 30 and second 32 solenoid valves to coordinate them so that the second 32 valve is closed when the first valve 30 is open and the first valve 30 is closed when the second valve 32 is open.

The DP cell 28 detects the pressure differential across the orifice 22 when the first solenoid valve 30 is open and the second solenoid valve 32 is closed. The DP cell 28 detects the pressure differential across the capillary tube 26 when the second solenoid valve 32 is open and the first solenoid valve 30 is closed. The DP cell 28 provides an electrical signal 34 in direct proportion to the measured pressure differential to the control system 36.

In the preferred embodiment, the control system 36 is an electrical system utilizing conventional switching techniques to operate the instrumentation in accordance with the procedures of the invention. If desired, the control system 36 may employ conventional solid state microprocessor techniques, such as: an electronic timing device or clock, an analog-to-digital converter, output signal amplifiers, storage memory for a control program, an arithmetic unit for dividing, and the like.

The present invention preferably employs a single DP cell 28, but using more than one DP cell 28 is possible. By using two DP cells 28, each DP cell 28 can individually monitor a separate pressure drop: one to continuously monitor the pressure drop across the orifice 22 and one to continuously monitor the pressure drop across the capillary tube 26. A single DP cell 28 is preferred, however, because it provides common mode rejection.

Referring to FIG. 1, zero offset error in the DP cell 28 can be completely eliminated by adding a line 42 with a third solenoid valve 44 for flowing sample gas 24 around the capillary tube 26. When the third 44 solenoid valve is opened, the pressure across the DP cell 28 is zero and the zero offset is the residual DP cell signal 34. The zero offset is communicated to the control system 36 where it is stored and subtracted from subsequent DP cell signals 34 taken when the third solenoid valve 44 is closed. In this manner, offset error is totally eliminated. The third solenoid valve 44 can be opened periodically for calibration.

A flow controller 40 for maintaining a substantially constant flow of sample gas 24 from the capillary tube 26 is located downstream of the capillary tube 26 and downstream from the branch 86 of the sample line where the second solenoid valve 32 is attached. Flow controllers are known in the art and an electronically adjustable pressure regulator followed by a capillary tube is suitable for this application. A pressure regulator 39 can be installed in the sample gas 24 line after the point 86 and before the flow controller 40 to reduce the pressure of the sample gas 24 at the flow controller 40.

The sample gas 24 must be maintained at a temperature substantially equal to the temperature of the pipeline gas 16 when it is in the capillary tube 26. If the temperature of the sample gas 24 is maintained at substantially the same temperature as the pipeline gas 16, the need to compensate the effects of supercompressibility can be avoided since gas density is maintained in the sample gas 24.

Figure 6:
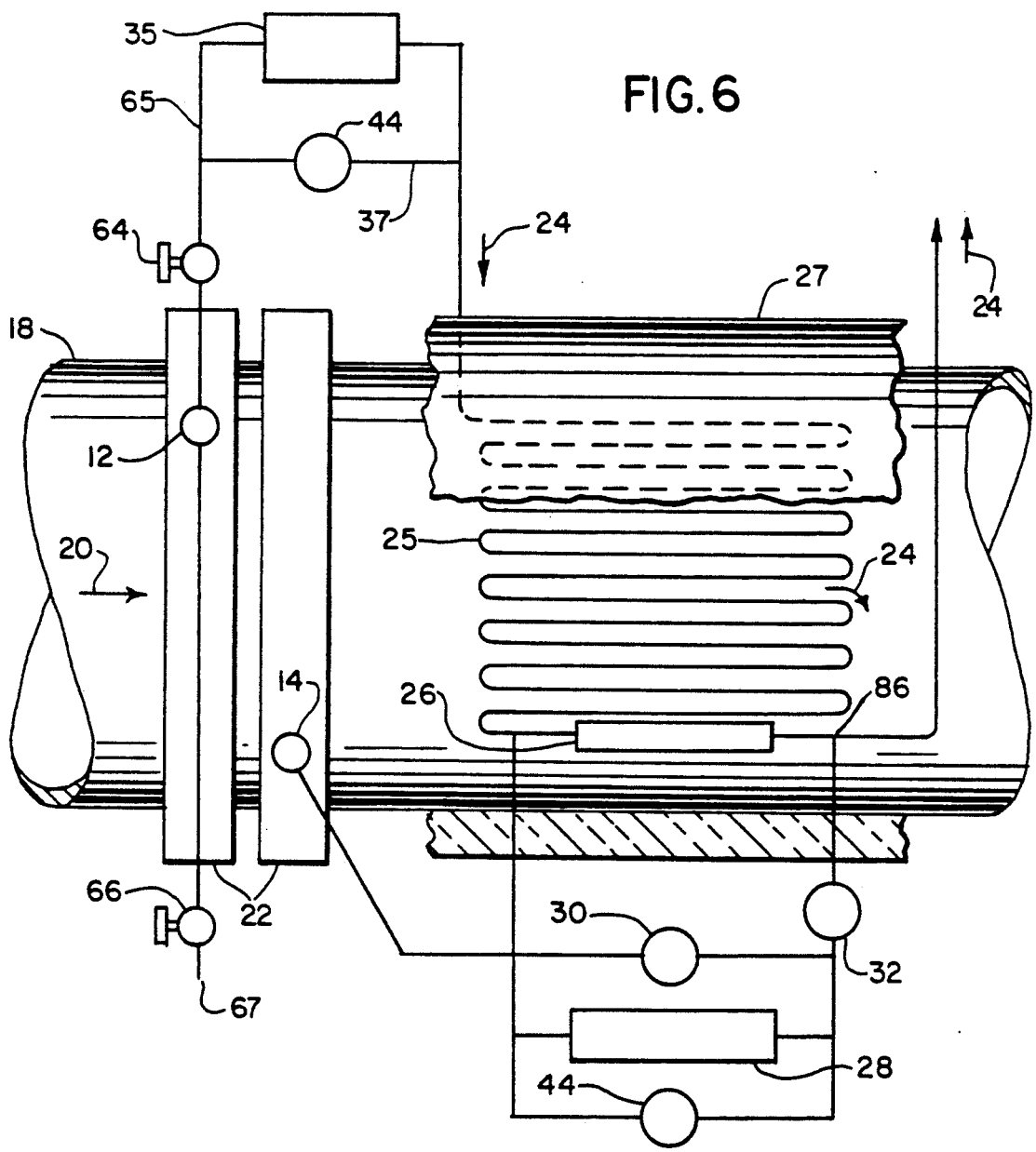
FIG. 6 is a schematic diagram showing the pipeline mounted components of the present invention.

Referring to FIG. 6, the preferred method of maintaining the proper sample gas 24 temperature within the capillary tube 26 involves routing the sample gas 24 to the capillary tube 26 through a serpentined line 25. Both the serpentined line 25 and the capillary tube 26 are mounted in intimate contact with the outside surface of the pipeline 18. Insulation 27 should be placed around the serpentined line 25, the capillary tube 26 and the pipeline 18 to facilitate temperature equalization. With this configuration, the temperature of the sample gas 24 within the capillary tube is maintained at substantially the same temperature as the temperature of the gas 16 flowing through the pipeline 18.

There are other, less preferred, methods for maintaining the proper sample gas 24 temperature within the capillary tube 26. One such method is to insert the capillary tube 26 into the pipeline 18.

It is not necessary to maintain the sample gas 24 temperature as substantially equal to the temperature of the gas 16 flowing through the pipeline 18 after the sample gas 24 exits the capillary tube 26. For that reason, the components of the invention which are not shown to be mounted on or at the pipeline 18 in FIG. 6 are pipeline mounted, but rather wall mounted.

An arching sample gas feed 65 along with a valve 64 and a valve 66 are used to remove debris entering the sample line at port 12. The low velocity in the rising section containing the valve 64 precludes particles from reaching the arch in the arching sample gas feed 65. Instead, the particles fall into a lower section of the pipe containing the valve 66. Periodically, the valve 66 can be opened to blow the collected debris from the lower section of the pipe through a blow hole 67.

A filter 35 is also installed on the arching sample gas feed 65 to remove debris from the sample gas 24 line. If the filter 35 becomes clogged, the invention may become ineffective so line 37 is installed around the filter 35 with an in-line solenoid valve 45. Periodically, valve 45 is opened, and the DP cell 28 in effect measures the additional pressure drop across the filter 35. The pressure drop across the filter 35 as measured can be used to correct the differential pressure valves across the capillary tube 26 that are measured by the DP cell 28 during operation. If the pressure drop across the filter 35 is too large, the filter should be replaced.

The mass flow rate of pipeline gas 16 through the orifice 22 in the pipeline 18 can be represented by:

$$\omega_o = F_o E_v Y_o C_o \sqrt{\rho_o \Delta P_o} \qquad (1)$$

where $F_o$ is the orifice 22 scaling constant, $E_v$ is the velocity approach factor, $Y_o$ is the expansion factor for the pipeline gas 16, $C_o$ is the orifice 22 discharge coefficient, $\rho_o$ is the density of the pipeline gas 16 and $\Delta P_o$ is the pipeline gas 16 pressure differential.

The orifice scaling constant, $F_o$, and the velocity approach factor, $$E_v = \left( \frac{1}{\sqrt{1 - \beta^4}} \right),$$

are constants that depend on orifice geometry. For example, $\beta$, for a circular orifice in a circular pipe, is defined as $d/D$ where $d$ is the diameter across the orifice and $D$ is the diameter of the pipe.

The gas expansion coefficient, $Y_o$, and the orifice discharge coefficient, $C_o$ in Eq. (1) can, however, vary with the pipeline gas 16 pressure or flow rate. The expansion coefficient, $Y_o$, for orifice 22 plates can be represented as:

$$Y_o = 1 - (0.41 + 0.35\beta^4) \frac{\Delta P_o}{k P_o},$$

where $P_o$ is the absolute pressure of the pipeline gas 16, and $k$ is the isentropic exponent of the gas 16.

The orifice discharge coefficient, $C_o$, is usually, and properly defined as a function of Reynold's Number, $$\left( R_e = \frac{\rho V D}{\mu}; \right.$$

where $\rho$ is gas density, V is flow velocity, D is the pipe diameter or other characteristic length of the flow field, and $\mu$ is the dynamic viscosity of the gas 16). The standard AGA-3 form for representing the discharge coefficient, $C_o$, is:

$$C_o = C_{io} + K_o \left[ \frac{1}{R_{eD}} \right]^{0.7} \qquad (3)$$

where $R_{eD}$ is the Reynold's Number of the pipeline gas 16 flow, $C_{io}$ represents the discharge coefficient at infinite $R_{eD}$ and $K_o$ is a coefficient for correction at finite $R_{eD}$.

In both Eqs. (2) and (3), the second terms are small compared to the first terms. In Eq. (2), the second term $$(0.41 + 0.35\beta^4) \frac{\Delta P_o}{k P_o}$$

is normally about 0.02 as compared to unity. In Eq. (3), the second term $$K_o \left( \frac{1}{R_{eD}} \right)$$

for most orifice installations is about 0.5% of $C_{io}$ or less.

The mass flow rate of the sample gas 24 through the capillary tube 26 is represented by:

$$\omega_c = F_c Y_c C_c \sqrt{\rho_c \Delta P_o} \qquad (4)$$

where $F_c$ is the capillary tube scaling constant, $Y_c$ is the sample gas 24 expansion factor, $C_c$ is the capillary tube discharge coefficient, $\rho_c$ is the density of the sample gas 24 in the capillary tube and $\Delta P_c$ is the sample gas 24 pressure differential as it flows through the capillary tube 26.

The form of Eq. (4) is similar to the form of Eq. (1), except that the approach velocity factor, $E_v$, which appears in Eq. (1) is taken to be unity in Eq. (4) because $\beta$ is very small for the capillary tube 26. The value of the capillary tube scaling constant, $F_c$, does not depend on the flow rate or pressure of the sample gas 24, but rather is a constant that depends on capillary tube 26 geometry.

The sample gas 24 expansion factor, $Y_c$, is represented by:

$$Y_c = 1 - 0.41 \frac{\Delta P_c}{k P_c} \qquad (5)$$

where $P_c$ is the absolute pressure of the sample gas 24, and k is the isentropic exponent of the sample gas 24. The form of Eq. (5) is similar to the form of Eq. (2), except that the $0.35\beta^4$ term in Eq. (2) is taken to be zero in Eq. (5) because $\beta$ is very small for the capillary tube 26.

It is preferred that the capillary tube 26 be a tortuous path capillary tube 26' as discussed above. The capillary tube discharge coefficient, $C_c$, for a tortuous path capillary tube 26' is represented by:

$$C_c = \frac{C_{ic}}{\sqrt{n}} + \frac{K_c}{\sqrt{n}} \left[ \frac{1}{R_{eC}} \right]^{0.7} \quad (6)$$

where $R_{eC}$ is the Reynold's Number of the sample gas 24 flow, n is the number of obstruction discs 58 within the tortuous path capillary tube 26', $C_{ic}$ represents a universal tortuous path capillary tube 26' discharge coefficient at infinite $R_{eC}$, and $K_c$ is a number for correction at finite $R_{eC}$.

As with Eqs. (2) and (3), the second term in Eqs. (5) and (6) are small compared to the first terms. The second term in Eq. (5), $$0.41 \frac{\Delta P_c}{k P_c}$$

is about 0.02 as compared to unity and the second term in Eq. (6), $$\frac{K_c}{\sqrt{n}} \left[ \frac{1}{R_{eD}} \right]^{0.7},$$

is about 5% of $$\frac{C_{ic}}{\sqrt{n}}.$$

The fact that the second terms in Eqs. (2), (3), (5) and (6) are much smaller than the first terms in these equations relaxes the necessary accuracy in determining the value of the second terms. For instance, a 10% error in determining a second term that has a value of only 2% of the first term results in an overall error of 0.2%. Testing has shown that Eq. (6) is very accurate for tortuous path capillary tubes 26'. Testing of tortuous path capillary tubes 26' also shows that the coefficients $C_{ic}$ and $K_c$ do not change with the number of obstruction discs 58 within the tortuous path capillary tube 26'.

The ratio of the mass flow rate of the pipeline gas 16, $\omega_o$, compared to the mass flow rate of the sample gas 24, $\omega_c$, is represented by dividing Eq. (1) by Eq. (4):

$$S = \frac{F_o E_v Y_o C_o \sqrt{\rho_o \Delta P_o}}{F_c Y_c C_c \sqrt{\rho_c \Delta P_c}} \quad (7)$$

where S is splitting variable that is $\omega_o/\omega_c$ if computed properly.

Since the pressure conditions across the orifice 22 in the pipeline 18 and across the capillary tube 26 are substantially equivalent and the sample gas 24 flowing through the tube 26 is maintained at substantially the same temperature as the pipeline gas 16, the density of the sample gas 24, $\rho_c$, is equal to the density of the pipeline gas 15, $\rho_o$. The splitting variable S can be represented by:

$$S = \frac{F_o E_v Y_o C_o \sqrt{\Delta P_o}}{F_c Y_c C_c \sqrt{\Delta P_c}}. \quad (8)$$

In Eq. (8), Fo, Fc, and $E_v$ are constants that can be determined from orifice 22 and capillary tube 24 geometry. The ratios $(Y_o/Y_c) = Y_r$, the gas expansion ratio, $(C_o/C_c) = C_r$, the discharge coefficient ratio, and $$\sqrt{\frac{\Delta P_o}{\Delta P_c}},$$

the differential pressure ratio depend on flow 20 conditions and are measured or calculated to solve Eq. (8) for the mass flow ratio.

In Clingman's U.S. Pat. Nos. 4,125,123; 4,396,299, and 5,016,482, the differential pressure ratio $$\sqrt{\frac{\Delta P_o}{\Delta P_c}}$$

in Eq. (8) is forced to unity by a flow controller. The present invention is different because it seeks to maintain the value of $\Delta P_c$ independent of the pipeline gas 16 pressure differential $\Delta P_o$ and measure the differential pressure ratio $$\sqrt{\frac{\Delta P_o}{\Delta P_c}}.$$

Since $\Delta P_c$ is independent of the pipeline gas 16 pressure differential $\Delta P_o$ in the present invention, difficulties related to fluctuating sample gas 24 flows through the capillary tube 26 are eliminated.

Referring still to Eq. (8), Clingman's U.S. Pat. No. 5,106,482 further employs a capillary tube constructed such that the expansion ratio, $(Y_o/Y_c) = Y_r$, is always nearly unity. The present invention does not require $Y_r = 1$. Rather, in the preferred embodiment, the present invention computes the ratio $(Y_o/Y_c) = Y_r$ by the following formula:

$$\left( \frac{Y_o}{Y_c} \right) = Y_r = \frac{1 - (0.41 + 0.35\beta^4)\frac{\Delta P_o}{k P_o}}{1 - 0.41 \frac{\Delta P_c}{k P_c}}. \quad (9)$$

As can be seen in FIG. 1, the absolute pressure of the gas 24 at the capillary tube 26, $P_c$, and the gas 16 at the orifice 22, $P_o$, are identical (i.e. $P_o = P_c$).

When pipeline 18 pressure is high (i.e. 400 to 1000 psia), $Y_r$ is nearly unity because $\Delta P_c$ and $\Delta P_o$ range from 0.3 to 4 or 5 psi. At lower pipeline 18 pressure, however, $Y_r$ might not be close to unity. $Y_r$ is, therefore, computed using Eq. (9). $\Delta P_c$ and $\Delta P_o$ are measured by the DP cell 28 and are needed to solve Eq. (9). The value of the isentropic coefficient, k, ranges from 1.2 to 1.4 for natural gas under the most extreme conditions. A value of 1.3 for k can therefore be used for solving Eq. (9) without causing substantial inaccuracies.

The absolute pipeline pressure $P_o = P_c$ must be determined to solve Eq. (9). Since Eq. (9) is a unity ratio with small correction terms in the numerator and denominator, it is sufficient that the absolute pipeline pressure, $P_o$, be determined to within 5 to 10% accuracy to maintain the accuracy in determining $Y_r$ to within a few percent. There are several methods for measuring the absolute pipeline pressure, $P_o$. One method is to use a pipeline mounted pressure transducer 88 as shown in phantom in FIG. 1. The pressure transducer 88 need not be accurate since the pressure value $P_o$ is used in the correction term in Eq. (9). Pressure transducers 88 suitable for this application are well known in the art and can be purchased from Honeywell, Precision Dynamics or other vendors.

If a tortuous path capillary tube 26' is used, which is preferred, the preferred method for determining the absolute pipeline pressure, $P_o$, and thus $Y_r$ through Eq. (9), requires a second tortuous path capillary tube 90 in connection with the flow controller 40.

Figure 7:
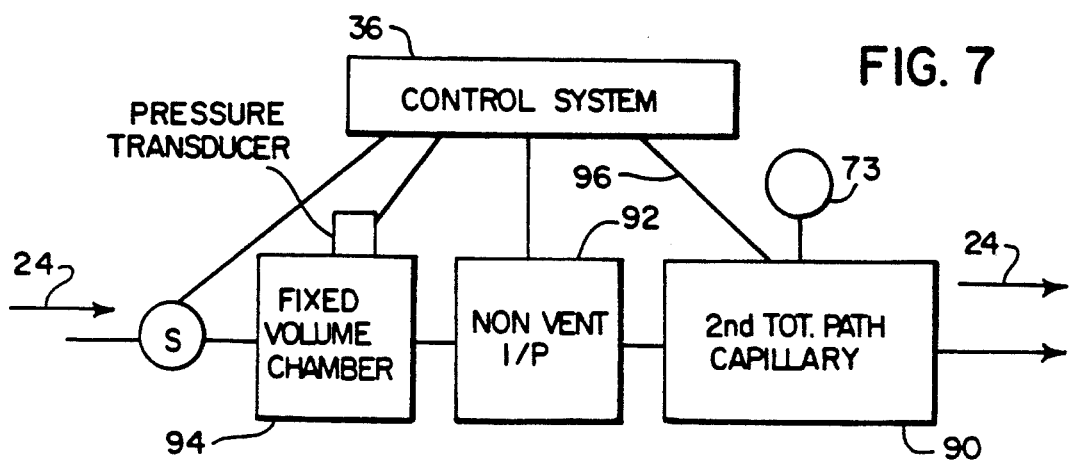
FIG. 7 is a schematic diagram showing apparatus for determining absolute pipeline pressure.

Referring to FIG. 7, a flow controller 40 has a second tortuous path capillary tube 90 for determining the absolute pipeline pressure, $P_o$, and an I/P converter 92. The flow controller 40 follows a molar flow meter 94. The molar flow meter 94 of the type described by Kennedy in U.S. Pat. No. 4,285,245 issued on Aug. 25, 1981 is appropriate for use with the flow controller 40. The sample gas 24 flows through the molar flow meter 94, the I/P converter 92 and the second tortuous path capillary tube 90 sequentially. In response to an electrical input signal 96 from the control system 36 (typically ranging from 4 to 20 ma direct current), the I/P converter 92 precisely determines the sample gas 24 pressure causing flow in a second tortuous path capillary tube 90.

Since the sample gas 24 composition is relatively consistent for the period of time it takes the sample gas 24 to flow through the system and the two tortuous path capillary tubes 26' and 90 are in series, the mass flow rate through the tortuous path capillary tube 26' mounted on the pipeline 18, $\omega_c$, is substantially equal to the mass flow rate through the second tortuous path capillary tube 90, $\omega_s$. Because the tortuous path capillary tube discharge coefficients, $C_c$, are identical for the two tortuous path capillary tubes, except for considerations of the number of obstruction discs 58 in each capillary tube, i.e. $n_c$ and $n_s$, the absolute pipeline pressure, $P_o$, can be represented by:

$$P_o = P_s \left(\frac{Z_c}{Z_s}\right)\left(\frac{n_c}{n_s}\right)\left(\frac{\Delta P_s}{\Delta P_c}\right)\left(\frac{Y_c^2}{Y_s^2}\right)\left(\frac{T_c}{T_s}\right) \quad (10)$$

where $(Z_c/Z_s)$ is the ratio of the compressibility factor of the sample gas 24 in the pipeline mounted tortuous path capillary tube 26' compared to the compressibility factor of the sample gas 24 in the second tortuous path capillary tube 90, $P_s$ is the absolute pressure of the sample gas 24 set by the I/P converter 92, $\Delta P_s$ is the pressure differential across the second tortuous path capillary tube 90 (i.e. $P_s - P_{atm}$). $Y_s$ is the gas expansion coefficient for the second tortuous path capillary tube 90, and $(T_c/T_s)$ is the ratio of the absolute sample gas 24 temperature in the pipeline mounted tortuous path capillary tube 26', $T_c$, compared to the absolute sample gas 24 temperature in the second tortuous path capillary tube 90, $T_s$.

In natural gas applications, the absolute temperature ratio $(T_c/T_s)$ is normally close to unity as determined on the absolute temperature scale. The pressure differential across the pipeline mounted tortuous path capillary tube 26', $\Delta P_c$, is determined by the DP cell 28. The absolute sample gas 24 pressure at the second tortuous path capillary tube 90, $P_s$, and the pressure differential across the second tortuous path capillary tube 90, $\Delta P_s$, are set contemporaneously by the I/P converter 92. The number of obstruction discs 58, $n_c$ and $n_s$, are known constants.

Figure 8:
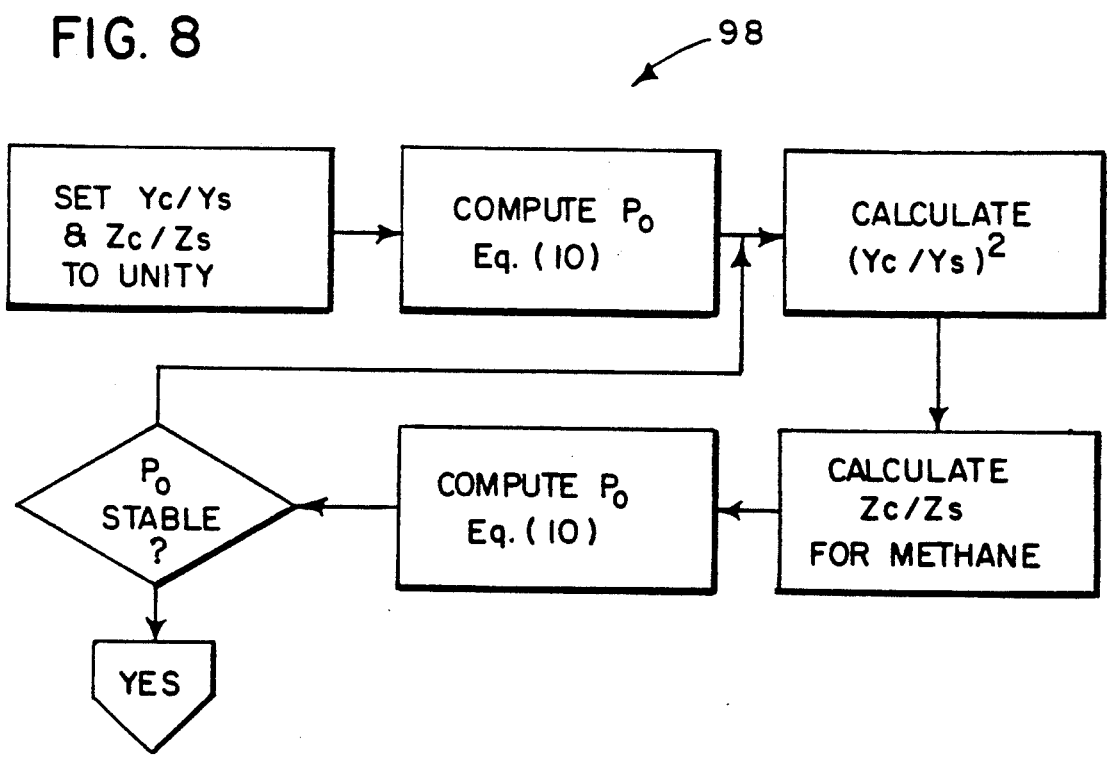
FIG. 8 is a flow diagram showing an iterative process for computing the absolute pipeline pressure.

Both the ratio of the compressibility factors $(Z_c/Z_s)$ and the ratio of the expansion factors $(Y_c^2/Y_s^2)$ are a function of the absolute pipeline pressure, $P_o$, so an iterative process 98 is used to solve Eq. 10 for $P_o$. The iterative process 98 is shown in FIG. 8. $P_o$ is first approximated by setting the ratios $(Z_c/Z_s)$ and $(Y_c^2/Y_s^2)$ equal to unity and computing Eq. (10). The expansion ratio $(Y_c^2/Y_s^2)$ is then computed using the following equation, which is similar to Eq. (9):

$$\left(\frac{Y_s}{Y_c}\right) = \frac{1 - (0.41)\frac{\Delta P_s}{kP_s}}{1 - 0.41\frac{\Delta P_c}{kP_c}} \quad (11)$$

Note that $\Delta P_c$ is measured by the DP cell 28 and $P_s$ and $\Delta P_s$ are set by the I/P converter 92.

The compressibility ratio $(Z_c/Z_s)$ in Eq. (10) is dependent on gas composition as well as gas pressure and temperature. Since accuracy requirements for Eq. (11) are not stringent and because natural gas normally contains 80% or more methane, the known virial coefficients of methane are used to compute the compressibility ratio $(Z_c/Z_s)$ without a significant loss in accuracy.

The absolute temperature ratio $(T_c/T_s)$ is very close to unity and can be assumed to be unity for the purposes of Eq. (10). Alternatively, the absolute temperatures, $T_c$ and $T_s$, can be measured by temperature detectors 72 and 73 shown in phantom in FIGS. 1 and 7.

After determining the absolute temperature ratio $(T_c/T_s)$ the expansion ratio $(Y_c^2/Y_s^2)$, and the compressibility ratio $(Z_c/Z_s)$, the control system 36 computes Eq. (10) for a new $P_o$ value and compares the new $P_o$ value to the previous $P_o$ value. If the newly computed pipeline pressure, $P_o$, differs from the previous $P_c$ value by more than 2%, the iterative process 98 shown in FIG. 8 is not complete and the process 98 continues by computing a new expansion ratio $(Y_c^2/Y_s^2)$ and compressibility ratio $(Z_c/Z_s)$ using the newly computed $P_o$ value. Iterative $P_o$ values are computed in this manner using the iterative process 98 until the computed $P_o$ value differs from the previously computed $P_o$ value by less than 2%.

Once the pipeline pressure $P_o$ is determined, the expansion factor ratio $Y_r = (Y_o/Y_c)$ needed to solve Eq. (8) is calculated according to Eq. (9).

In order to solve Eq. (8) for the splitting variable S, the discharge coefficient ratio $(C_o/C_c) = C_r$ must also be determined. The orifice discharge coefficient, $C_o$, is defined in Eq. (3) and the capillary tube 26 discharge coefficient, $C_c$, is defined in Eq. (6). The capillary tube 26 discharge coefficient, $C_c$, can be determined by using the control system 36 to periodically vary the flow of the sample gas stream between two preselected flows. The flow controller 40 as shown in FIG. 7, is used to measure the molar flow ratio of the sample gas stream 24. As discussed above, it is appropriate to use the type of molar flow meter 94 described by Kennedy in U.S. Pat. No. 4,285,245.

Pseudo discharge coefficients, based on the molar flows, can be represented for the two preselected flows by:

$$Y_1 C_1^* = \frac{\omega_1^*}{\sqrt{\rho_c \Delta P_{c1}}} \quad (12a)$$

$$Y_2 C_2^* = \frac{\omega_2^*}{\sqrt{\rho_c \Delta P_{c2}}} \quad (12a)$$

where $C_1^*$ and $C_2^*$ are pseudo discharge coefficients for the capillary tube 26 at the two preselected sample gas 24 flows $\omega_1^*$ and $\omega_2^*$. The molar flows $\omega_1^*$ and $\omega_2^*$ are determined in the molar flow meter 94 by measuring the time, $tm_1$ and $tm_2$ for the pressure in a fixed volume 95 to drop between two predetermined pressures. Accepting that $\omega_1^*$ and $\omega_2^*$ can be represented by $tm_1$ and $tm_2$ and dividing Eq. (12a) by Eq. (12b) results in:

$$\frac{Y_1 C_1^*}{Y_2 C_2^*} = \frac{tm_1}{tm_2} \sqrt{\frac{\Delta P_{c2}}{\Delta P_{c1}}} . \quad (13)$$

The ratio of the pseudo capillary tube discharge coefficients $$\frac{Y_1 C_1^*}{Y_2 C_2^*}$$

is assumed to be equal to the ratio of the actual capillary tube discharge coefficients $$\frac{Y_1 C_1}{Y_2 C_2}$$

for the two preselected flows, so:

$$\frac{Y_1 C_1}{Y_2 C_2} = \frac{tm_1}{tm_2} \sqrt{\frac{\Delta P_{c2}}{\Delta P_{c1}}} = \frac{Y_1}{Y_2} \frac{C_i + K_c f(R_{e1})}{C_i + K_c f(R_{e2})} \quad (14)$$

where $R_{e1}$ and $R_{e2}$ are the Reynold's Numbers for the flow through the capillary tube 26 at the preselected flows. If the capillary tube 26 is a tortuous path capillary tube 26', which is preferred, the $K_c f(R_e)$ term in Eq. (14) is small compared to the $C_i$ term for the normal range of operating Reynold's Number. Moreover, the two preselected flows can be set in a ratio such that $R_{e2} = \eta R_{e1}$. The function $f(R_{e1})$, is then represented by:

$$f(R_{e1}) = \frac{C_i \frac{Y_2}{Y_1} \frac{tm_2}{tm_1} \sqrt{\frac{\Delta P_{c2}}{\Delta P_{c1}}} - 1}{1 - \frac{1}{\eta^{0.7}}} . \quad (15)$$

Equation (15) allows the calculation of the function $f(R_{e1})$ in real time without knowing the viscosity, $\mu$, of the sample gas 24.

The ratio of the Reynold's Number of the flow through the tortuous path capillary tube 26' compared to the flow through the orifice 22 is represented by:

$$\frac{R_{eD}}{R_{eC}} = S \frac{D_D}{D_C} \quad (16)$$

where $D_C$ is the effective diameter of the tortuous path capillary tube 26' mounted on the pipeline 18 and $D_D$ is the effective diameter of the pipeline 18. It follows that the discharge coefficient ratio, $(C_o/C_c) = C_r$ is determined by solving Eq. (17) by iteration:

$$\left(\frac{C_o}{C_c}\right) = C_r = \frac{C_{ic}\left[1 + \frac{K_c \frac{Y_2}{Y_1} \sqrt{\frac{\Delta P_{c2}}{\Delta P_{c1}}} - 1}{1 - \frac{1}{\eta^{0.7}}}\right]}{C_{io}\left[1 + \left(S \frac{D_D}{D_C}\right)\right]^{0.7} \frac{K_o \frac{C_{ic}}{C_{io}} \frac{Y_2}{Y_1} \sqrt{\frac{\Delta P_{c2}}{\Delta P_{c1}}} - 1}{1 - \frac{1}{\eta^{0.7}}}} . \quad (17)$$

Equation (17) is solved by iteration because the solution to Eq. (17) depends on the splitting variable S and S as defined in Eq. (8) depends on $C_o/C_o = Cr$. After the discharge coefficient ratio $(C_o/C_c) = C_r$ is determined by iteration, the splitting variable S is calculated in the control system 36 pursuant to Eq. (8). The splitting variable S represents the mass flow rate $\omega_c/\omega_o$.

Figure 9:
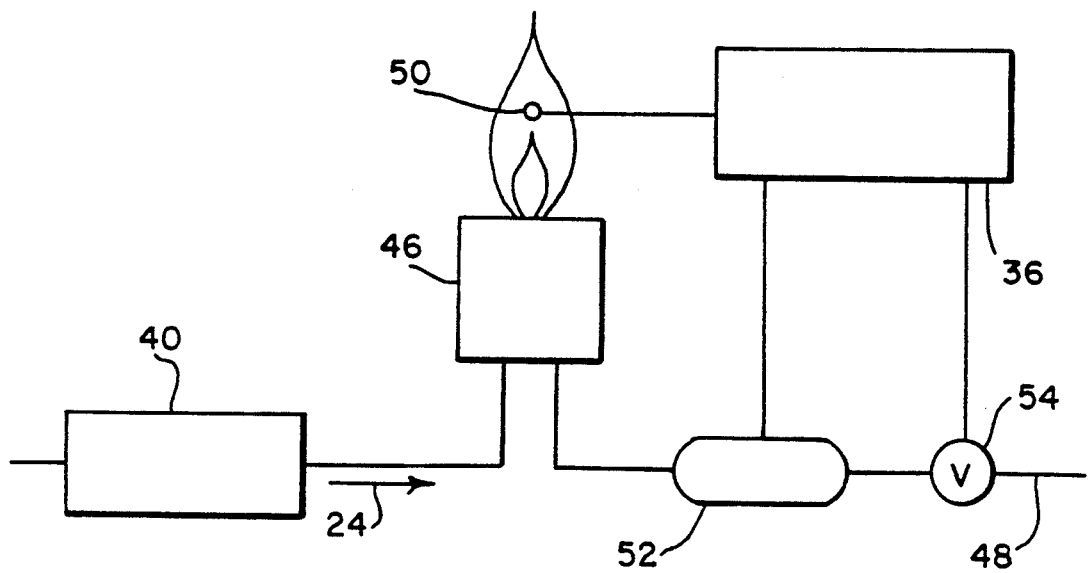
FIG. 9 is a schematic drawing showing additional apparatus of the present invention for measuring the energy flow rate of the gas through the pipeline.

Referring generally to FIG. 9, the invention described above can be used with the invention described hereafter, which is much like the method and apparatus described by Clingman in U.S. Pat. No. 4,125,123 issued on Nov. 14, 1978 for determining the energy content of the flow of pipeline gas 16. For saturated hydrocarbon gas, the amount of air required to completely combust gas at maximum flame temperature, i.e. stoichiometric combustion, is precisely proportional to the energy released during combustion. If the gas being combusted is a saturated hydrocarbon, the energy flow rate of the sample gas 24 is represented by:

$$\frac{\partial E_c}{\partial t} = K_{sto} \omega_{air} \quad (18)$$

where $K_{sto}$ is the stoichiometric proportionality constant, and $\omega_{air}$ is the air flow rate. Likewise, the energy flow rate of the pipeline gas 16 through the pipeline 18 is represented by:

$$\frac{\partial E_o}{\partial t} = H \omega_o \quad (19)$$

In light of Eqs. (8) and (18), Eq. (19) can be rewritten as:

$$\frac{\partial E_o}{\partial t} = K_b \omega_{air} \left(\frac{C_o}{C_c}\right)\left(\frac{Y_o}{Y_c}\right) \sqrt{\frac{\Delta P_o}{\Delta P_c}} \quad (20)$$

where $K_b$ is a constant.

In accordance with Eq. (20), the apparatus shown in FIG. 9 determines the energy flow rate of the pipeline gas 16 passing through the pipeline 18.

Referring in particular to FIG. 9, sample gas 24 flows to a burner 46 after it leaves the flow controller 40. Air is supplied to the burner 46 by an air hose 48 and the sample gas 24 burns above the burner 46. A thermocouple 50 which communicates to the control system 36 monitors flame temperature. The air flowing through the air hose 48 is monitored by an air mass flow meter 52. Air mass flow meters are old in the art and are accurate at ambient conditions. The air flow is adjusted by an air valve 54, which also communicates with the control system 36, until the sample gas 24 burns at maximum flame temperature. When the flame burns at the maximum flame temperature, the energy flow rate of the pipeline gas 16 can be determined.

The energy flow rate of the pipeline gas 16 is calculated in the control system 36 in accordance with Eq. (20). The ratios ($C_o/C_c$) and ($Y_o/Y_c$) are computed by the means discussed above. The value $K_b$ is a constant and is stored in the control system 36. The other valves in Eq. (20), $\omega_{air}$, the air mass flow rate measured by the air flow meter 52, and $\Delta P_o$ and $\Delta P_c$, pressure drops measured by the DP cell 28, are communicated electronically to the control system 36 periodically.

Since the sample gas 24 is supplied to the burner 46 at a substantially constant mass flow rate, flame lift is minimized and the flame temperature is measured accurately. Burning at a substantially constant mass flow rate is the present mode of the PMI (Precision Machine Products, Inc. Dallas, Tex.) GB-2000 series of products and has operated successfully for over 15 years.

Many modifications and variations of the preferred embodiment which are within the spirit and scope of the invention will be apparent to those with ordinary skill in the art.

I claim:

1. An apparatus for measuring a ratio of a mass flow rate of a pipeline gas flowing through a pipeline compared to a mass flow rate of a sample gas tapped from the pipeline, the pipeline having a first device means for producing a pipeline gas pressure differential, the apparatus comprising:

a second device means for producing a sample gas pressure differential while maintaining the sample gas at substantially the same temperature as the pipeline gas;

means for routing the sample gas to the second device means;

means for measuring the pipeline gas pressure differential as the pipeline gas flows through the first device means;

means for measuring the sample gas pressure differential as the sample gas flows through the second device means;

a flow controlling means located downstream of the second device means for maintaining a sample gas flow rate through the second device means independent of the pipeline gas pressure differential; and a control means for comparing the sample gas pressure differential with the pipeline gas pressure differential in order to obtain the mass flow rate ratio.

2. An apparatus as recited in claim 1 further comprising a pressure regulator located downstream of the second device means and upstream of the flow controlling means for reducing the pressure of the sample gas before it flows to the flow controlling means.

3. An apparatus as recited in claim 1 wherein the control means determines the mass flow ratio in accordance with the following function:

$$\frac{\omega_o}{\omega_c} = K \frac{Y_o C_o \sqrt{\Delta P_o}}{Y_c C_c \sqrt{\Delta P_c}}$$

where K is a constant, $Y_o$ is the expansion factor for the pipeline gas, $C_o$ is the discharge coefficient for the first device means, $Y_C$ is the sample gas expansion factor, $C_C$ is the discharge coefficient for the second device means, $\Delta P_o$ is the pressure differential of the pipeline gas across the first device means in the pipeline and $\Delta P_c$ is the pressure differential of the sample gas across the second device means.

4. An apparatus as recited in claim 3 wherein the flow controlling means periodically varies the sample gas molar flow rate between two preselected molar flow rates and the apparatus further comprises a sample gas flow meter located downstream of the second device means and upstream of the flow controlling means.

5. An apparatus as recited in claim 3 wherein the second device means is a first tortuous path capillary tube.

6. An apparatus as recited in claim 5 wherein the flow controlling means has a second tortuous path capillary tube.

7. An apparatus as recited in claim 3 further comprising a pressure transducer to measure the absolute pipeline pressure $P_O$ to determine the ratio of the expansion factor for the pipeline gas, $Y_o$, compared to the sample gas expansion factor, $Y_C$.

8. An apparatus for measuring the energy flow rate of a pipeline gas through a pipeline, the pipeline having a first device means for producing a pipeline gas pressure differential, the apparatus comprising:

a second device means for producing a sample gas pressure differential which maintains the sample gas at substantially the same temperature as the pipeline gas;

means for routing the sample gas to the second device means;

means for measuring the pipeline gas pressure differential as the pipeline gas flows through the first device means;

means for measuring the sample gas pressure differential as the sample gas flows through the second device means;

a flow controlling means located downstream of the second device means for maintaining a sample gas flow rate through the second device means that is independent of the pipeline gas pressure differential;

means for determining the energy flow rate of the sample gas; and a control means for comparing the sample gas pressure differential with the pipeline gas pressure differential in order to obtain a mass flow rate ratio of the pipeline gas to sample gas and for obtaining the energy flow rate of the pipeline gas from the energy flow rate of the sample gas and the mass flow rate ratio.

9. An apparatus as recited in claim 8 wherein the means for determining the energy flow rate of the sample gas comprises:

a burner for burning the sample gas with air to form a flame; and a means for maximizing the flame temperature.

10. An apparatus as recited in claim 9 further comprising an air mass flow meter for measuring the air mass flow rate of the air burning the sample gas.

11. An apparatus as recited in claim 10 wherein the control means determines the energy flow rate of the pipeline gas in accordance with the following function:

$$\frac{\partial E_o}{\partial t} = K \omega_{air} \frac{Y_o C_o \sqrt{\Delta P_o}}{Y_c C_c \sqrt{\Delta P_c}}$$

where K is a constant, $\Delta P_O$ is the pipeline gas pressure differential, $\Delta P_c$ is the sample gas pressure differential, $Y_o$ is the expansion factor for the pipeline gas, $C_o$ is the discharge coefficient for the first device means, $Y_C$ is the sample gas expansion factor, $C_C$ is the discharge coefficient the second device means, and $\omega_{air}$ is the air mass flow rate.

12. A method for measuring a mass flow rate ratio of a pipeline gas through a pipeline compared to a sample gas tapped from the pipeline, the method comprising the steps:

measuring a pipeline gas pressure differential as the pipeline gas flows across a first device located within the pipeline for producing the pipeline gas pressure differential;

flowing the sample gas to a second device for producing a sample gas pressure differential;

maintaining the temperature of the sample gas in the second device at substantially the same temperature as the pipeline gas in the pipeline;

maintaining a substantially constant sample gas mass flow rate through the second device independent of the pipeline gas pressure differential;

measuring the sample gas pressure differential as the sample gas flows across the second device; and determining the mass flow rate ratio by comparing the pipeline gas pressure differential to the sample gas pressure differential.

13. A method as recited in claim 12 wherein the second device is a capillary tube and a control system is used to determine the mass flow rate ratio in accordance with the following function:

$$\frac{\omega_o}{\omega_c} = K \frac{Y_o C_o \sqrt{\Delta P_o}}{Y_c C_c \sqrt{\Delta P_c}}$$

where K is a constant, $Y_o$ is the expansion factor for the pipeline gas, $C_o$ is the discharge coefficient for the first device, $Y_C$ is the sample gas expansion factor, $C_C$ is the discharge coefficient for the second device, $\Delta P_o$ is the pressure differential of the pipeline gas across the first device in the pipeline and $\Delta P_c$ is the pressure differential of the sample gas across the second device.

14. A method as recited in claim 13 further comprising the step of periodically varying the sample gas molar flow rates between two preselected molar flow rates to determine the ratio ($C_o/C_r$).

15. A method as recited in claim 13 wherein the second device is a first tortuous path capillary tube and further comprising the step of flowing the sample gas to a second tortuous path capillary tube after the sample gas flows through the first tortuous path capillary tube to estimate the absolute pipeline pressure $P_o$ for determining the ratio $Y_o/Y_c$.

16. A method as recited in claim 13 wherein the ratio of the expansion factor for the pipeline gas, $Y_o$ compared to the sample gas expansion factor, $Y_C$, is a function of the absolute pipeline pressure $P_O$ and further comprising the step of measuring the absolute pipeline pressure $P_O$.

17. A method for measuring the energy flow rate of a pipeline gas through a pipeline, the method comprising:

measuring a pipeline gas pressure differential as the pipeline gas flows across a first device located within the pipeline for producing the pipeline gas pressure differential;

flowing the sample gas to a second device for producing a sample gas pressure differential;

maintaining the temperature of the sample gas in the second device at substantially the same temperature as the pipeline gas in the pipeline;

maintaining a sample gas mass flow rate through the second device independent of the pipeline gas pressure differential;

measuring the sample gas pressure differential as the sample gas flows across the second device;

measuring the energy flow rate of the sample gas;

determining a mass flow rate ratio of the pipeline gas to the sample gas by comparing the pipeline gas pressure differential to the sample gas pressure differential; and determining the energy flow rate of the pipeline gas from the energy flow rate of the sample gas and the mass flow rate ratio.

18. A method as recited in claim 17 wherein the energy flow rate of the sample gas is measured by:

burning the sample gas with air after the sample gas flows through the second device; and adjusting the air flow so that the sample gas burns at maximum flame temperature.

19. A method as recited in claim 18 further comprising the step of measuring the air mass flow rate of air burning the sample gas.

20. A method as recited in claim 19 wherein a control system is used to determine the energy flow rate of the pipeline gas in accordance with the following function:

$$\frac{\partial E_o}{\partial t} = K \omega_{air} \frac{Y_o C_o \sqrt{\Delta P_o}}{Y_c C_c \sqrt{\Delta P_c}}$$

where K is a constant, $\Delta P_O$ is the pipeline gas pressure differential, $\Delta P_c$ is the sample gas pressure differential, $Y_o$ is the expansion factor for the pipeline gas, $C_o$ is the discharge coefficient for the first device, $Y_C$ is the sample gas expansion factor, $C_C$ is the discharge coefficient the second device, and $\omega_{air}$ is the air mass flow rate.

21. An apparatus for measuring a ratio of a mass flow rate of a pipeline gas flowing through a pipeline compared to a mass flow rate of a sample gas tapped from the pipeline, the pipeline having a first device means for producing a pipeline gas pressure differential, the apparatus comprising:

a second device means for producing a sample gas pressure differential while maintaining the sample gas at substantially the same temperature as the pipeline gas;

a first line connected to the pipeline upstream of the first device means for routing the sample gas to the second device means;

a differential pressure cell means for alternately measuring the pipeline gas pressure differential as the pipeline gas flows across the first device means and the sample gas pressure differential as the sample gas flows through the second device means;

a flow controlling means for maintaining a sample gas flow rate through the second device means independent of the pipeline gas pressure differential;

a second line for routing the sample gas away from the second device means to the flow controlling means;

a pressure regulator located in the second line for reducing the sample gas pressure before the sample gas flows to the flow controlling means;

a third line for routing the sample gas away from the flow controlling means; and a control means for receiving data from the differential pressure cell means and computing the ratio of the mass flow rate of the pipeline gas through the pipeline compared to the mass flow rate of the sample gas through the second device means.

22. An apparatus as recited in claim 21 further comprising a pressure transducer mounted to the pipeline and in communication with the control means for measuring the absolute pipeline pressure to determine the ratio of the mass flow rates.

23. An apparatus as recited in claim 22 wherein the flow controlling means periodically varies the sample gas molar flow rate between two preselected molar flow rates and the apparatus further comprises a sample gas flow meter for measuring the flow through the second line.

24. An apparatus for measuring the energy flow rate of a pipeline gas through a pipeline, the pipeline having a first device means for producing a pipeline gas pressure differential, and the apparatus comprising:

a second device means for producing a sample gas pressure differential while maintaining the sample gas at substantially the same temperature as the pipeline gas;

a first line connected to the pipeline upstream of the first device means for routing the sample gas to the second device means;

a differential pressure cell means for alternately measuring the pipeline gas pressure differential as the pipeline gas flows across the first device means and the sample gas pressure differential as the sample gas flows through the second device means;

a flow controlling means for maintaining a sample gas flow rate through the second device means independent of the pipeline gas pressure differential;

a second line for routing the sample gas away from the second device means to the flow controlling means;

a pressure regulator located in the second line for reducing the sample gas pressure before the sample gas flows to the flow controlling means;

a burner for burning the sample gas with an air flow to form a flame;

a third line for routing the sample gas away from the flow controlling means to the burner;

a temperature sensor for measuring flame temperature;

an air conduit for routing the air flow to the burner;

an air valve located in the air conduit for adjusting the air flow through the air conduit;

an air mass flow meter for measuring an air mass flow rate through the air conduit; and a control means for receiving data from the differential pressure cell means, the air mass flow meter and the temperature sensor, for communicating with the air valve to adjust the air flow so that the flame burns at the maximum temperature, and for computing the energy flow rate of the pipeline gas through the pipeline.

25. An apparatus as recited in claim 24 further comprising a pressure transducer mounted on the pipeline and in communication with the control means for measuring the absolute pipeline pressure to determine the energy flow rate of the pipeline gas through the pipeline.

26. An apparatus as recited in claim 24 wherein the flow controlling means periodically varies the sample gas molar flow rate between two preselected molar flow rates and the apparatus further comprises a sample gas flow meter for measuring the flow through the second line.

27. A volumetric flow corrector to be used with a differential pressure flowmeter measuring a volumetric flow rate and a pressure differential of a pipeline gas flowing through a pipeline, that monitors the energy flow rate of the pipeline gas flowing through the pipeline, and represents the flow of the pipeline gas in terms of an adjusted volumetric flow rate that corresponds to a volumetric flow rate at a defined pressure and temperature, the volumetric flow corrector comprising:

a pressure reduction device means for producing a sample gas pressure differential which maintains the sample gas at substantially the same temperature as the pipeline gas;

means for routing the sample gas to the pressure reduction device means;

means for measuring the sample gas pressure differential as the sample gas flows through the pressure reduction device means;

a flow controlling means located downstream of the pressure reduction device for maintaining a sample gas flow rate through the pressure reduction device means that is independent of the pipeline gas pressure differential;

a sample gas energy flow rate meter;

means for determining the energy content per unit volume of the sample gas; and a control means for comparing the sample gas pressure differential with the pipeline gas pressure differential, and for calculating the adjusted volumetric flow rate of the pipeline gas through the pipeline from the volumetric flow rate measured by the differential pressure flowmeter from the ratio of sample gas pressure differential compared to the ratio of the pipeline gas pressure differential, the energy flow rate of the sample gas, and the energy content per unit volume of the sample gas.

28. A method for monitoring the energy flow rate of a pipeline gas through a pipeline and representing the flow of the pipeline gas in terms of an adjusted volumetric flow rate which corresponds to a volumetric flow rate at a defined pressure and temperature, the method comprising:

measuring a pipeline gas pressure differential and a volumetric flow rate with a differential pressure meter;

flowing sample gas to a pressure reduction device for producing a sample gas pressure differential;

maintaining the temperature of the sample gas in the pressure reduction device at substantially the same temperature as the pipeline gas in the pipeline;

maintaining a sample gas mass flow rate through the pressure reduction device independent of the pipeline gas pressure differential;

measuring the sample gas pressure differential as the sample gas flows across the pressure reduction device;

comparing the sample gas pressure differential to the pipeline gas pressure differential;

measuring the energy flow rate of the sample gas;

measuring the energy content per unit volume of the sample gas; and calculating the adjusted volumetric flow rate of the pipeline gas through the pipeline from the volumetric flow rate of the pipeline gas measured by the differential pressure meter, the ratio of the sample gas pressure differential to the pipeline gas pressure differential, the energy flow rate of the sample gas, and the energy content per unit volume of the sample gas.

29. An apparatus for measuring a ratio of a mass flow rate of a pipeline gas flowing through a pipeline compared to a mass flow rate of a sample gas tapped from the pipeline, the pipeline having an orifice through which the pipeline gas flows, the apparatus comprising:

a conduit for flowing sample gas tapped from the pipeline;

a capillary located in the conduit, the sample gas being maintained at substantially the same temperature as the pipeline gas when the sample gas flows through the capillary;

means for measuring a pipeline gas pressure differential as a pipeline gas flows through the orifice;

means for measuring a sample gas pressure differential as a sample gas flows through the capillary;

a flow controller located in the conduit downstream of the capillary to maintain a flow rate of the sample gas flowing through the capillary independently of the pipeline gas pressure differential; and a control means for comparing the sample gas pressure differential with the pipeline gas pressure differential in order to obtain the mass flow rate ratio.

* * * * *